(«12») United States Patent
Yamashita (10) Patent No.: US 8,233,698 B2
(45) Date of Patent: Jul. 31, 2012

(54) PATTERN INSPECTION APPARATUS, CORRECTED IMAGE GENERATION METHOD, AND COMPUTER-READABLE RECORDING MEDIUM STORING PROGRAM

(75) Inventor: Kyoji Yamashita, Kanagawa (JP)

(73) Assignees: Kabushiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 1240 days.

(21) Appl. No.: 11/971,550

(22) Filed: Jan. 9, 2008

(65) Prior Publication Data

US 2008/0260234 A1 Oct. 23, 2008

(30) Foreign Application Priority Data

Mar. 19, 2007 (JP) ................................. 2007-070398

(51) Int. Cl.
*G06K 9/00* (2006.01)
(52) U.S. Cl. .................. 382/149; 382/218; 382/275
(58) Field of Classification Search .............. 356/237.2, 356/394; 382/141, 145, 149, 218, 274
See application file for complete search history.

(56) References Cited

U.S. PATENT DOCUMENTS

| | | | |
|---|---|---|---|
| 6,396,943 B2 * | 5/2002 | Yamashita | 382/144 |
| 6,835,511 B2 * | 12/2004 | Hirayanagi | 430/22 |
| 6,865,288 B1 * | 3/2005 | Shishido et al. | 382/145 |
| 7,095,884 B2 * | 8/2006 | Yamaguchi et al. | 382/145 |
| 7,142,708 B2 * | 11/2006 | Sakai et al. | 382/149 |
| 7,268,803 B1 * | 9/2007 | Murata et al. | 348/218.1 |
| 7,417,723 B2 * | 8/2008 | Hamamatsu et al. | 356/237.2 |
| 7,590,277 B2 * | 9/2009 | Oaki et al. | 382/141 |
| 2005/0196033 A1 * | 9/2005 | Hamamatsu et al. | 382/149 |
| 2007/0165941 A1 * | 7/2007 | Shinohara et al. | 382/149 |
| 2007/0177787 A1 * | 8/2007 | Maeda et al. | 382/141 |
| 2008/0018874 A1 * | 1/2008 | Dusa et al. | 355/55 |

FOREIGN PATENT DOCUMENTS

| | | |
|---|---|---|
| JP | 11-153550 | 6/1999 |
| JP | 2003-107669 | 4/2003 |

OTHER PUBLICATIONS

M. Takagi et al., "Handbook on Image Analysis", University of Tokyo Press, Jan. 17, 1991, pp. 442-443. (with Partial English Translation).

* cited by examiner

*Primary Examiner* — Gregory M Desire
(74) *Attorney, Agent, or Firm* — Oblon, Spivak, McClelland, Maier & Neustadt, L.L.P.

(57) ABSTRACT

A pattern inspection apparatus includes a first unit configured to acquire an optical image of a target workpiece to be inspected, a second unit configured to generate a reference image to be compared, a third unit configured, by using a mathematical model in which a parallel shift amount, an expansion and contraction error coefficient, a rotation error coefficient, a gray-level offset and an image transmission loss ratio are parameters, to calculate each of the parameters by a least-squares method, a forth unit configured to generate a corrected image by shifting a position of the reference image by a displacement amount, based on the each of the parameters, and a fifth unit configured to compare the corrected image with the optical image.

13 Claims, 6 Drawing Sheets

PATTERN INSPECTION APPARATUS, CORRECTED IMAGE GENERATION METHOD, AND COMPUTER-READABLE RECORDING MEDIUM STORING PROGRAM

CROSS-REFERENCE TO RELATED APPLICATION

This application is based upon and claims the benefit of priority from the prior Japanese Patent Application No. 2007-070398 filed on Mar. 19, 2007 in Japan, the entire contents of which are incorporated herein by reference.

BACKGROUND OF THE INVENTION

1. Field of the Invention

The present invention relates to a pattern inspection apparatus, a image registration method, or a computer program for applying the method. For example, the present invention is applicable to a pattern inspection technique that inspects a pattern defect on a mask pattern or a master pattern used in fabricating semiconductor devices, and an inspection apparatus that detect a defect on fine patterns of a photomask, a wafer and a liquid crystal substrate (LCD).

2. Description of Related Art

In recent years, a LSI line-width required for semiconductor devices has been shrinking to tens of nanometers. These semiconductor devices are manufactured by exposing or projecting a circuit pattern on a wafer by using a reduction-magnification exposure projection apparatus such as a stepper while using a master pattern (called a mask or a reticle, and will be called a mask hereinafter) on which a circuit pattern is written. Therefore, in order to fabricate a mask for projecting fine circuit patterns on a wafer, a pattern writing apparatus is employed that writes a fine circuit pattern. Alternatively, a circuit pattern could be directly written onto a wafer by the writing apparatus. In addition to an electron beam writing apparatus, a laser beam writing apparatus might be also applicable.

Since LSIs require enormous fabrication cost, an improvement in yield is crucial in semiconductor business. However, line-width of LSI has been shrinking downto tens of nanometers. The yield loss in semiconductor devices is significantly due to a pattern defect on a mask. In particular, critical-dimension (CD) error is so detrimental that much tighter CD uniformity is necessary. Therefore, a pattern inspection apparatus which inspects those defects is necessary to guarantee the quality of a mask.

As to a conventional pattern inspection apparatus, the following is known as pattern inspection methods: 'die-to-die inspection' that compares optical image data obtained by capturing images of the same patterns at different positions on the same mask, and 'die-to-database inspection' that inputs writing data (CAD data) which is generated by converting GDSII data to be input by a writing apparatus, generates a reference image based on the inputted writing data, and compares a reference image with an optical image obtained by capturing the image of the pattern. In the inspecting methods of the inspection apparatus, a target workpiece is placed on a stage to be scanned by a flux of light while the stage is moving to scan the workpiece.

The target workpiece is irradiated with a flux of light from a light source and an illumination optics system. Light transmitted through the target workpiece or reflected by the target workpiece is focused on a sensor through an optical system. The image captured by the sensor is transmitted to a comparison circuit as measurement data. In the comparison circuit, after registration of the images, the measurement data is compared with reference data based on an appropriate comparison algorithm. When the measurement data is significantly different from the reference data, it is judged to be a pattern defect.

In order to perform inspection as described above, image registration between a reference image and an optical image is strictly required. It is, therefore, preferable to correct only systematic position errors, such as stage misplacement due to an error due to expansion and contraction, and a rotation error along the axis of an X-Y stage. In other words, it is preferable not to correct errors that are local and random, such as a pattern defect. Performing correcting as described above is required for detecting minute defects.

As a image registration method, for example, a technique is disclosed that calculates an amount of displacement and a sum of gray level differences between a reference image and an optical image by using a least-squares method (refer to, e.g., Japanese Unexamined Patent Publication No. 11-153550 (JP-A-11-153550)). For example, as shown in the equation (1) below, there is a mathematical model in which an optical image is represented by shifting and interpolating the reference image by the amount of misalignment. In the equation (1), S (x, y) shows a gray level of an optical image, and U (x, y) shows a gray level of a reference image. Parameters to calculate are the amount of shift: $(x_0, y_0)$, an offset of gray level: $\epsilon_0$, and an image transmission loss ratio: $\epsilon_1$. However, since this mathematical model is based on a simple shift, it is not sufficient to compensate a placement error from image distortion, and/or rotation.

$$S(x,y) = -\epsilon_0 + (1-\epsilon_1) \cdot U(x-x_0, y-y_0) \qquad (1)$$

The following equation (2) can be obtained by calculating a linear approximation of the equation (1). The unknown parameter has four degrees of freedom.

$$\epsilon_0 + \epsilon_1 U + x_0 \cdot \partial U/\partial x + y_0 \cdot \partial U/\partial y = U - S \qquad (2)$$

Further, a method that interpolates the target image data by use of image data of four neighboring points of the image data is described in a reference (refer to, e.g., Image Analysis Handbook, at pp. 442 to 443, University of Tokyo Press, first edition issued on Jan. 17, 1991).

As to the equation (2), a solution, which is not heretofore known, can be considered as follows: Normalizing the size of an image frame to 1 and interpolating target image data by use of a bilinear interpolation method of the four points stated above, the equation (2) can be modeled to the following equation (3).

$$\begin{aligned} U - S = &(1-x) \cdot (1-y) \cdot (\varepsilon_0^{(1)} + \varepsilon_1^{(1)} U + x_0^{(1)} \cdot \partial U/\partial x + y_0^{(1)} \cdot \partial U/\partial y) + \\ &x \cdot (1-y) \cdot (\varepsilon_0^{(2)} + \varepsilon_1^{(2)} \cdot U + x_0^{(2)} \cdot \partial U/\partial x + y_0^{(2)} \cdot \partial U/\partial y) + \\ &x \cdot y \cdot (\varepsilon_0^{(3)} + \varepsilon_1^{(3)} \cdot U + x_0^{(3)} \cdot \partial U/\partial x + y_0^{(3)} \cdot \partial U/\partial y) + \\ &(1-x) \cdot y \cdot (\varepsilon_0^{(4)} + \varepsilon_1^{(4)} \cdot U + x_0^{(4)} \cdot \partial U/\partial x + y_0^{(4)} \cdot \partial U/\partial y) \end{aligned} \qquad (3)$$

As shown in the equation (3), adding this interpolation scheme makes it possible to correct the placement error resulting from image distortion, and/or rotation which is not sufficient to be corrected by using the model of the equations (1) and (2). However, a four-point weighted interpolation scheme increases necessary parameters to 16 (four times the above-mentioned model) and calculation time accordingly, as shown in the equation (3). Furthermore, in addition to the problem of increasing the number of the unknown parameters, there exists another problem that instability in the calculation result occurs when the in case for sparse figure density is sparse.

BRIEF SUMMARY OF THE INVENTION

In accordance with one aspect of the present invention, a pattern inspection apparatus includes
an optical image acquisition unit configured to acquire an optical image of a target workpiece to be inspected on which a pattern is formed, a reference image generation unit configured to generate a reference image to be compared with the optical image,
a least-squares method calculation unit configured, by using a mathematical model in which a parallel shift displaced from a position where the optical image and the reference image are aligned by a pixel unit, an image distortion error (expansion and contraction error coefficient), a rotation error coefficient, a gray-level offset and a ratio of image transmission loss are parameters, to calculate each of the parameters by a least-squares method, a corrected image generation unit configured to generate a corrected image by shifting a position of the reference image by a displacement amount displaced from the position aligned pixel by pixel, based on the each of the parameters, and a comparison unit configured to compare the corrected image with the optical image.

In accordance with another aspect of the present invention, a pattern inspection apparatus includes an optical image acquisition unit configured to acquire an optical image of a target workpiece to be inspected on which a pattern is formed, a reference image generation unit configured to generate a reference image to be compared with the optical image, a least-squares method calculation unit configured, by using a mathematical model in which a parallel shift displaced from a position where the optical image and the reference image are aligned by pixel by pixel, an expansion and contraction error coefficient, a rotation error, a gray-level offset and a ratio of image transmission loss are parameters, to calculate each of the parameters by a least-squares method, a judgment unit configured to judge whether a calculated parallel shift, a calculated expansion and contraction error coefficient, a calculated rotation error coefficient, a calculated_gray-level offset and a calculated image transmission loss ratio are suitable or unsuitable, by using each threshold value set up for each of the parameters, a second least-squares method calculation unit configured to delete at least one parameter judged to be unsuitable or set up a value equivalent to deletion for the parameter judged to be unsuitable, and recalculate other parameters in the mathematical model by the least-squares method, a corrected image generation unit configured to generate a corrected image by shifting a position of the reference image by a displacement displaced from the position aligned by the pixel unit, based on recalculated parameters, and a comparison unit configured to compare the corrected image with the optical image.

Furthermore, in accordance with another aspect of the present invention, a corrected image generation method includes inputting an optical image and a reference image of a target workpiece to be inspected, calculating, by using a mathematical model in which a parallel shift amount displaced from a position where the optical image and the reference image are aligned by a pixel unit, an expansion and contraction error coefficient, a rotation error coefficient, a gray-level offset and an image transmission loss ratio are parameters, the parameters by a least-squares method, and generating a corrected image by shifting a position of the reference image by a displacement amount displaced from the position aligned by the pixel unit, based on calculated parameters, and outputting the corrected image.

Moreover, in accordance with another aspect of the present invention, a corrected image generation method includes inputting an optical image and a reference image of a target workpiece to be inspected, calculating, by using a mathematical model in which a parallel shift amount displaced from a position where the optical image and the reference image are sparsely aligned by a pixel unit, an expansion and contraction error coefficient, a rotation error coefficient, a gray-level offset and an image transmission loss ratio are parameters, the parameters by a least-squares method, judging whether a calculated parallel shift amount, a calculated expansion and contraction error coefficient, a calculated rotation error coefficient, a calculated gray-level offset and a calculated image transmission loss ratio are suitable or unsuitable by using each threshold value set up for each of the parameters, deleting at least one parameter judged to be unsuitable or setting up a value equivalent to deletion for the parameter judged to be unsuitable, and recalculating other parameters in the mathematical model by a least-squares method, and generating a corrected image by shifting a position of the reference image by a displacement amount displaced from the position aligned by the pixel unit, based on recalculated parameters, and outputting the corrected image.

Moreover, in accordance with another aspect of the present invention, a computer-readable recording medium storing a program to be executed by a computer, the program includes storing an optical image and a reference image to be used for a comparative inspection of a target workpiece to be inspected on which a pattern is formed, in a storage device, reading the optical image and the reference image from the storage device, and by using a mathematical model in which a parallel shift amount displaced from a position where the optical image and the reference image are aligned by a pixel unit, an expansion and contraction error coefficient, a rotation error coefficient, a gray-level offset and an image transmission loss ratio are parameters, calculating the parameters by a least-squares method, and generating a corrected image by shifting a position of the reference image by a displacement amount displaced from the position aligned by the pixel unit, based on the parameters, and outputting the corrected image.

Furthermore, in accordance with another aspect of the present invention, a computer-readable recording medium storing a program to be executed by a computer, the program includes storing an optical image and a reference image to be used for a comparative inspection of a target workpiece to be inspected on which a pattern is formed, in a storage device, reading the optical image and the reference image from the storage device, and by using a mathematical model in which a parallel shift amount displaced from a position where the optical image and the reference image are aligned by a pixel unit, an expansion and contraction error coefficient, a rotation error coefficient, a gray-level offset and an image transmission loss ratio are parameters, calculating the parameters by a least-squares method, judging whether a calculated parallel shift amount, a calculated expansion and contraction error coefficient, a calculated rotation error coefficient, a calculated gray-level offset and a calculated image transmission loss ratio are suitable or unsuitable by using each threshold value set up for each of the parameters, deleting at least one parameter judged to be unsuitable or setting up a value equivalent to deletion for the parameter judged to be unsuitable, and recalculating other parameters in the mathematical model by a least-squares method, and generating a corrected image by shifting a position of the reference image by a displacement amount displaced from the position aligned by the pixel unit, based on recalculated parameters, and outputting the corrected image.

DETAILED DESCRIPTION OF THE INVENTION

Embodiment 1

According to Embodiment 1, there will be described an inspection apparatus that performs a highly accurate position alignment by an operation using parameters of decreased number, and a method of generating a corrected image obtained by correcting a reference image to be at a position highly precisely aligned.

Figure 1:
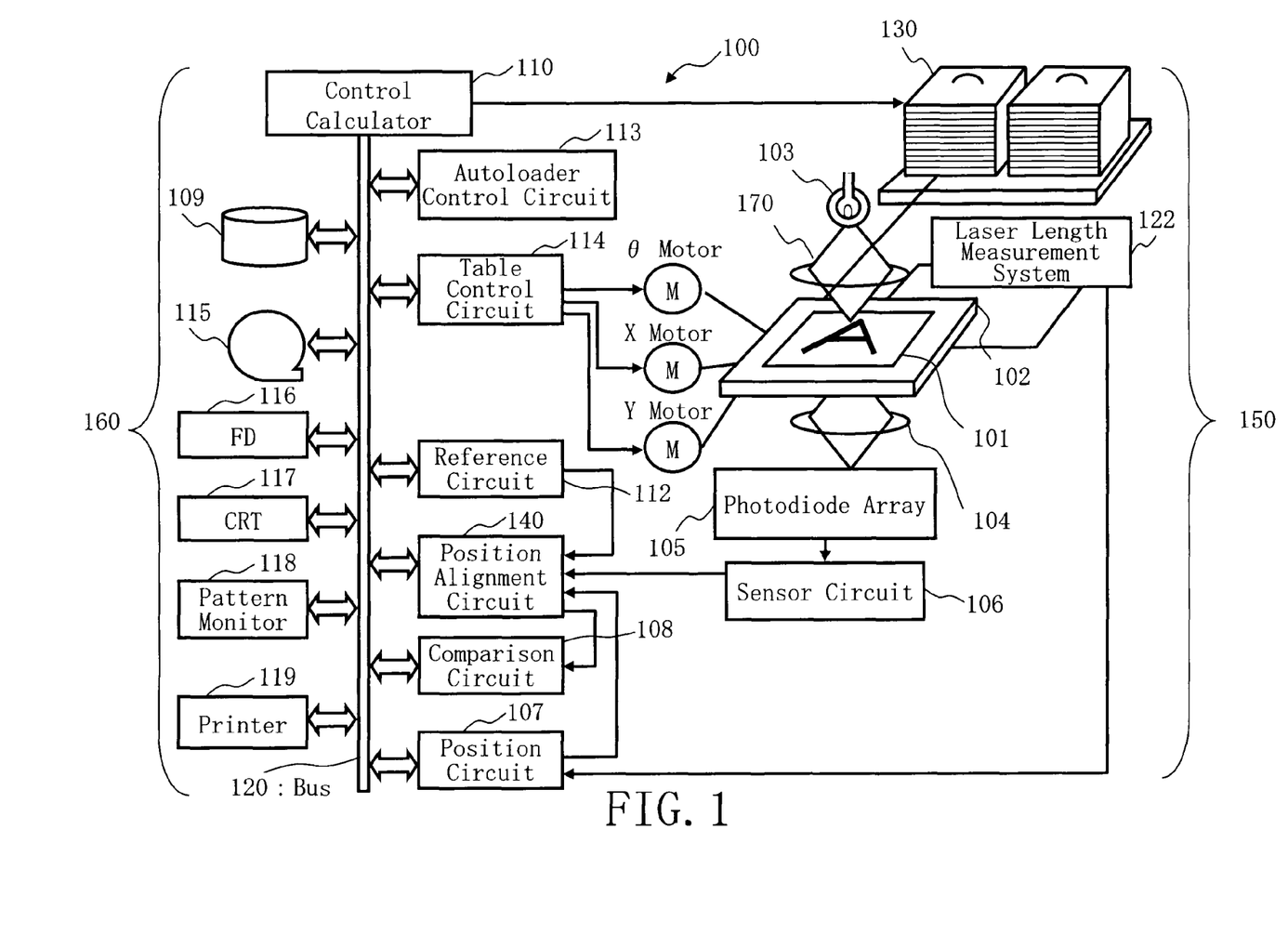
FIG. 1 is a schematic diagram showing the structure of a pattern inspection apparatus according to Embodiment 1.

FIG. 1 is a schematic diagram showing the structure of a pattern inspection apparatus described in Embodiment 1. As shown in FIG. 1, a pattern inspection apparatus 100 that inspects a defect of a substrate, such as a mask or a wafer, serving as a target workpiece includes an optical image acquisition unit 150 and a control system circuit 160. The optical image acquisition unit 150 includes an XYθ table 102, a light source 103, a magnification optical system 104, a photodiode array 105, a sensor circuit 106, a laser length measurement system 122, an autoloader 130, and an illumination optical system 170. In the control system circuit 160, a control calculator 110 serving as a computer is connected, through a bus 120 serving as a data transmission path, to a position circuit 107, a comparison circuit 108, a reference circuit 112 being an example of a reference image generation unit, an alignment circuit 140, an autoloader control circuit 113, a table control circuit 114, a magnetic disk drive 109, a magnetic tape drive 115, a flexible disk drive (FD) 116, a CRT 117, a pattern monitor 118, and a printer 119. The XYθ table 102 is driven by an X-axis motor, a Y-axis motor, and a θ-axis motor. In FIG. 1, only configuration elements necessary for explaining Embodiment 1 are described, and others are not described. It should be understood that other elements generally necessary for the pattern inspection apparatus 100 are included.

Figure 2:
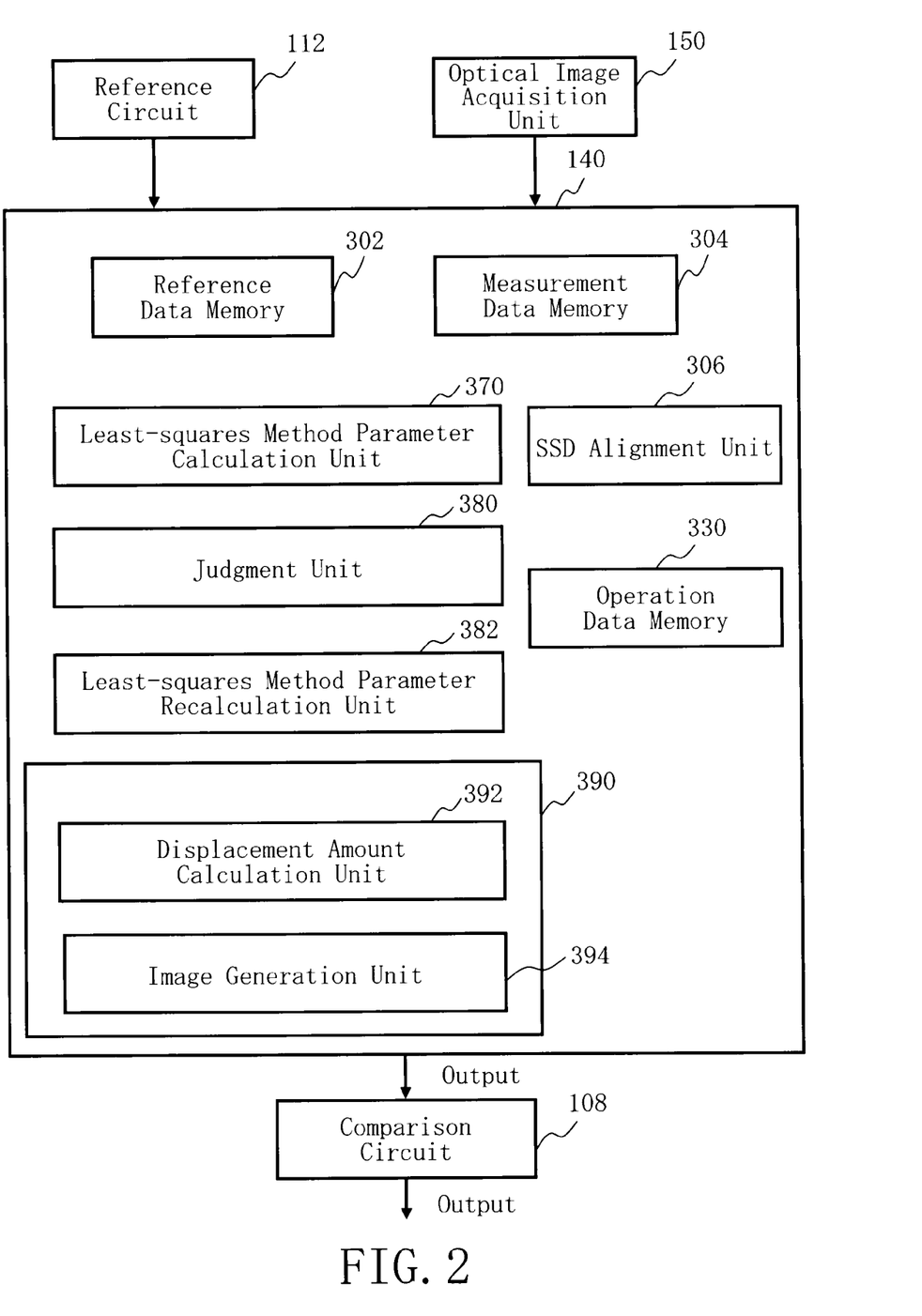
FIG. 2 is a block diagram showing a configuration of an alignment circuit according to Embodiment 1.

FIG. 2 is a block diagram showing an example of the configuration of an alignment circuit described in Embodiment 1. As shown in FIG. 2, the alignment circuit 140 includes a reference data memory 302, a measurement data memory 304, an SSD (Sum of the Squared Difference) alignment unit 306, an operation data memory 330, a least-squares method parameter calculation unit 370, a judgment unit 380, a least-squares method parameter recalculation unit 382, and a corrected image generation circuit 390. The corrected image generation circuit 390 includes a displacement amount calculation unit 392 and an image generation unit 394. The alignment circuit 140 inputs reference data (reference image) from the reference circuit 112 and measurement data (optical image) from the optical image acquisition unit 150, generates a corrected image by performing a position alignment, and outputs corrected image data and measurement data to the comparison circuit 108. The data etc. operated in the alignment circuit 140 is stored in the operation data memory 330 as needed.

Figure 3:
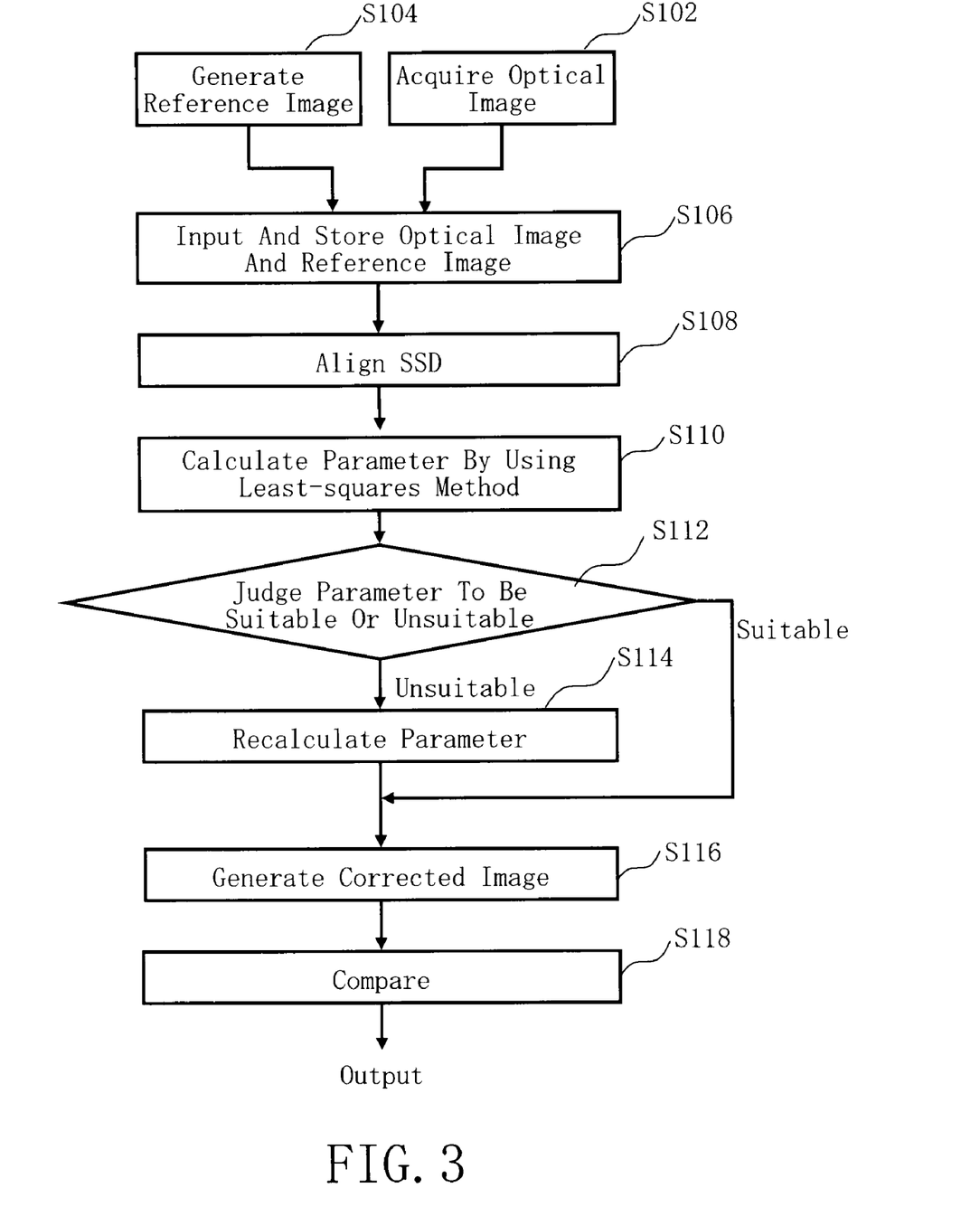
FIG. 3 is a flowchart showing main steps of a pattern inspection method according to Embodiment 1.

FIG. 3 is a flowchart showing main steps of a pattern inspection method described in Embodiment 1. As shown in FIG. 3, the pattern inspection method executes a series of steps including an optical image acquisition step (S102), a reference data generation step (S104), an input & storage step (S106), an SSD alignment step (S108), a least-squares method parameter calculation step (S110), a judgment step (S112), a least-squares method parameter recalculation step (S114), a corrected image generation step (S116), and a comparison step (S118).

In S (step) 102, as the optical image acquisition step, the optical image acquisition unit 150 acquires an optical image of a photomask 101 serving as the target workpiece on which a figure indicated by figure data included in design data is written based on the design data.

Specifically, the optical image is acquired as follows: The photomask 101 to be inspected is placed on the XYθ table 102 which is movable in a horizontal direction and a rotating direction by the X-, Y-, and θ-axis motors. The pattern written on the photomask 101 is irradiated with lights from the appropriate light source 103 arranged above the XYθ table 102. The photomask 101 serving as a target workpiece is irradiated with a flux of light from the light source 103 through the illumination optical system 170. Below the photomask 101, the magnification optical system 104, the photodiode array 105, and the sensor circuit 106 are arranged. The light transmitted through the photomask 101 serving as a target workpiece such as an exposure mask is focused on the photodiode array 105 as an optical image through the magnification optical system 104 and enters the photodiode array 105.

Figure 4:
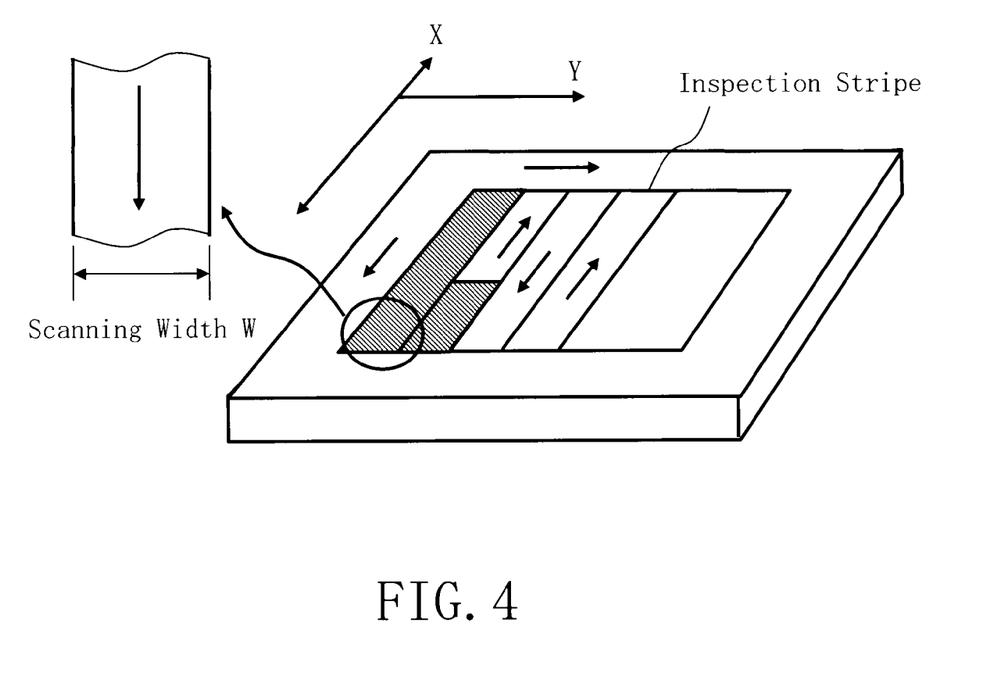
FIG. 4 shows a diagram for describing a procedure for acquiring an optical image according to Embodiment 1.

FIG. 4 shows a diagram for describing a procedure for acquiring an optical image described in Embodiment 1. As shown in FIG. 4, a region to be inspected is virtually divided into a plurality of strip-like inspection stripes, each of which has a scanning width W, in the Y direction. To acquire an optical image, the movement of the XYθ table 102 is controlled so that each of the divided inspection stripes can be continuously scanned, while moving in the X direction. In the photodiode array 105, images each having the scanning width W as shown in FIG. 4 are continuously input. After the image on the first inspection stripe having been acquired, the image similarly having the scanning width W on the second inspection stripe is continuously input while moving in the reverse direction. When acquiring the image on the third inspection stripe, the image is scanned while moving in the direction reverse to the one for scanning the image on the second inspection stripe, i.e., the same direction as the one for scanning the image on the first inspection stripe. Continuously acquiring images in this manner makes it possible to reduce wasteful processing time.

The image of the pattern focused on the photodiode array 105 is photoelectrically converted by the photodiode array 105, and furthermore, A/D converted (analog to digital converted) by the sensor circuit 106. In the photodiode array 105, a sensor such as a TDI sensor is arranged. By continuously moving the XYθ table 102 serving as a stage in the X-axis direction, the TDI sensor captures the image of the pattern of the photomask 101 serving as a target workpiece. An inspection optical system having a large magnification is composed of the light source 103, the magnification optical system 104, the photodiode array 105, and the sensor circuit 106.

The XYθ table 102 is driven by the table control circuit 114 under the control of the control calculator 110. The XYθ table 102 can be moved by the drive system such as a three-axis (X-Y-θ) motor which drives the XYθ table 102 in the X direction, the Y direction, and the θ direction.

Measurement data (optical image) output from the sensor circuit 106 is transmitted to the alignment circuit 140 together with data output from the position circuit 107 and indicating the position of the photomask 101 on the XYθ table 102. The measurement pattern data is 8-bit unsigned data, for example, and indicates a gray level of brightness of each pixel. The measurement data is compared with each image data of 512×512 pixels, for example.

Then, in step S104, as the reference data generation step, the reference circuit 112 generates reference data (reference image) which is to be compared with measurement data, based on the design data of the photo mask 101 serving as a target workpiece to be inspected. The reference data to be compared is generated as image data of 512×512 pixels, for example, like the measurement data.

The reference data herein is generated based on the design data in order to execute a "die to database inspection", but it is not restricted thereto. A "die to die inspection" can also be conducted, and in this case, reference data can be generated based on another measurement data (optical image) to be used for comparison.

Next, as the alignment step, position alignment is performed in order to compare the measurement data with the reference data. Concretely, corrected image data is generated by correcting the reference data to be in accordance with the position of the measurement data.

In step 106, as the input & storage step, each reference data, 512×512 pixels for example, is read using the control calculator 110 and stored in the reference data memory 302. In the same manner, each measurement data, 512×512 pixels for example, is read and stored in the measurement data memory 304.

In step 108, as the SSD alignment step, the SSD alignment unit 306 calculates an amount to be displaced, by shifting per pixel unit, from a position sparsely aligned by the first pixel unit to a position where the sum of squared difference between a measurement data pixel value and a reference data pixel value becomes the minimum. As the position sparsely aligned according to the first pixel unit, a position indicated by the data coordinate system may be used.

First, the SSD alignment unit 306 reads reference data of an image region (frame) of a predetermined size, which is to be a unit of measurement for comparison processing, from the reference data memory 302 on the basis of positional information from the position circuit 107. In this case, the SSD alignment unit 306 generates images (displaced images), shifted in parallel by a pixel unit, for each reference data of a frame. Then, measurement data is compared with each reference data in the frame. For example, as mentioned above, it is preferable to define a region of 512×512 pixels as one frame. The sum of squared difference is calculated between each piece of a plurality of reference data obtained by shifting by a pixel unit and measurement data of the same region size read from the measurement data memory 304. Concretely, the sum of squared difference can be calculated by squaring the residual between each pixel value of the reference data and each pixel value of the measurement data, and summing the squared residuals in the whole region which has been read. The sum of squared difference is calculated for each of the plurality of reference data, and their minimum value is obtained. Then, the measurement data and the reference data are aligned to the position where the minimum value is obtained. The aligned measurement data and reference data are stored in the operation data memory 330. Although the position alignment is carried out based on a pixel unit in the above, it is also suitable to perform shifting per sub-pixel unit, and align the measurement data and the reference data to the position where the sum of squared difference between a measurement data pixel value and a reference data pixel value becomes the minimum. For example, 1/8, 1/16, 1/32, etc. of one pixel can be a sub-pixel unit.

Figure 5:
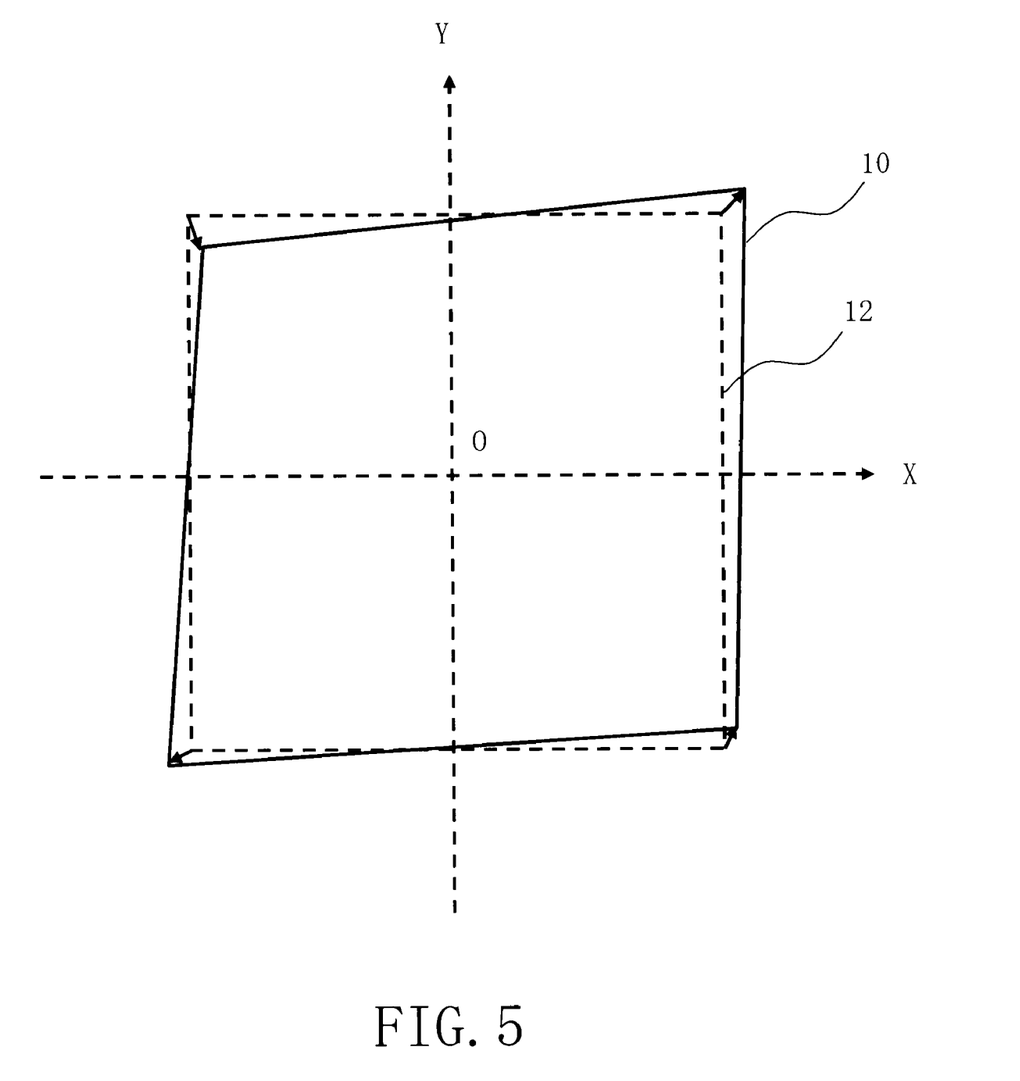
FIG. 5 shows an example of reference data and measurement data according to in Embodiment 1.

FIG. 5 shows an example of the reference data and the measurement data described in Embodiment 1. In the measurement data 10, an error due to expansion and contraction and an error due to rotation occur as mentioned above with respect to the reference data 12 in addition to a parallel shift error and a gray level change error. FIG. 5 shows an example of the measurement data 10 which has been deformed due to these errors. Therefore, in order to perform highly accurate alignment, it is necessary to correct the error due to expansion and contraction and the error due to rotation in addition to correcting the parallel shift error and the gray level change error.

Then, the inventor of the present invention found that the following model equations (4-1) to (4-3) can correct an expansion and contraction and a rotation in addition to a parallel shift and a gray level change. It is herein defined that $S(x, y)$ indicates a gray level value (pixel value) of an optical image, $U(x, y)$ indicates a gray level value (pixel value) of a reference image, and unknown parameters are a parallel shift amount $(x_0, y_0)$, a constant $\epsilon_0$ of gray level change, an image transmission loss ratio $\epsilon_1$ of gray level change, an expansion and contraction error coefficient $\delta x$ in the X direction, an expansion and contraction error coefficient $\delta y$ in the Y direction, a rotation error coefficient $\theta$ in the X direction, and a rotation error coefficient $\phi$ in the Y direction.

$$S(x,y) = -\epsilon_0 + (1-\epsilon_1)\cdot U(x-X', y-y') \quad (4\text{-}1)$$

$$x' = x - (x-x_0)\cdot(1+\delta_0)\cdot\cos\theta + (y-y_0)\cdot(1+\delta_y)\cdot\sin\theta \quad (4\text{-}2)$$

$$y' = y - (y-y_0)\cdot(1+y_0)\cdot\cos\phi - (x-x_0)\cdot(1+\delta_x)\cdot\sin\phi \quad (4\text{-}3)$$

Since the degree of freedom of the equation (3) of the 4-point weighted model mentioned above is 16, it turns out that the displacement amount due to expansion and contraction, and rotation can be modeled by 8 degrees of freedom which is half of 16. Assuming that the eight parameters of the equations (4-1) to (4-3) are sufficiently small, the equation (5) can be obtained by calculating a linear approximation of the equation (4).

$$\varepsilon_0 + \varepsilon_1 U + x_0 \cdot \partial U/\partial x + y_0 \cdot \partial U/\partial y - \delta_x \cdot (x \cdot \partial U/\partial x) - \delta_y \cdot (y \cdot \partial U/\partial y) + \theta \cdot (y \cdot \partial U/\partial x) - \phi \cdot (x \cdot \partial U/\partial y) = U - S \quad (5)$$

Furthermore, the unknown parameter x of 8 degrees of freedom can be obtained by solving Ax=b by using A, x, and b that are expressed by the following equations (6-1) to (6-5).

$$A = (\Sigma u_{ij}^T \cdot u_{ij}) \quad (6\text{-}1)$$

$$b = (\Sigma y_{ij}) \quad (6\text{-}2)$$

$$x = (\epsilon_0, \epsilon_1, x_0, y_0, \delta_x, \delta_y, \theta, \phi) \quad (6\text{-}3)$$

$$u_{ij} = (1, U_{ij}, (\partial U_{ij}/\partial x), (\partial U_{ij}/\partial y), (-x \cdot \partial U_{ij}/\partial x), (-y \cdot \partial U_{ij}/\partial y), (y \cdot \partial U_{ij}/\partial x), (-x \cdot \partial U_{ij}/\partial y)) \quad (6\text{-}4)$$

$$y_{ij} = (U_{ij} - S_{ij}) \cdot u_{ij} \quad (6\text{-}5)$$

In step 110, as the least-squares method parameter calculation step, the least-squares method parameter calculation unit 370 calculates each parameter of the model equation (5) by a least-squares method, using the model equations (5) and (6-1) to (6-5).

That is, the least-squares method parameter calculation unit 370 calculates a gray-level offset $\epsilon 0$, an image transmission loss ratio $\epsilon_1$, a parallel shift amount $\epsilon_0$ in the X direction, a parallel shift amount $y_0$ in the Y direction, an expansion and contraction error coefficient $\delta x$ in the X direction, an expansion and contraction error coefficient $\delta y$ in the Y direction, a rotation error coefficient $\theta$ in the X direction, and a rotation error coefficient $\phi$ in the Y direction so that they can satisfy the relation that a first difference is equal to a second difference.

The first difference is obtained by subtracting a second sum from a first sum.

The first sum is the sum of a gray-level offset $\epsilon 0$, a product of an image transmission loss ratio $\epsilon_1$ and a pixel value U(x, y) of the reference image, a product of a parallel shift amount $x_0$ in the X direction and a value obtained by partially differentiating (space differentiation) the pixel value U(x, y) of the reference image with respect to x, a product of a parallel shift amount $y_0$ in the Y direction and a value obtained by partially differentiating the pixel value U(x, y) of the reference image with respect to y, and a product of a rotation error coefficient $\theta$ in the X direction, a value obtained by partially differentiating the pixel value U(x, y) of the reference image with respect to x, and a variable y.

The second sum is the sum of a product of an expansion and contraction error coefficient $\delta x$ in the X direction, a value obtained by partially differentiating the pixel value U(x, y) of the reference image with respect to x, and a variable x, a product of an expansion and contraction error coefficient $\delta y$ in the Y direction, a value obtained by partially differentiating the pixel value U(x, y) of the reference image with respect to y, and the variable y, and a product of a rotation error coefficient $\phi$ in the Y direction, a value obtained by partially differentiating the pixel value U(x, y) of the reference image with respect to y, and the variable x.

The second difference is obtained by subtracting a pixel value S(x, y) of an optical image from the pixel value U(x, y) of the reference image.

Thus, since the number of unknown parameters is decreased to eight, the operation time can be shortened by this decreased amount.

However, all these parameters cannot be necessarily stably obtained in all the patterns. For example, in the case of a sparse pattern with a low pattern density and a one-dimensional pattern such as a line & space, there is a possibility of having an unstable solution when the model equations (5) and (6-1) to (6-5) are solved as they are. Then, the following judgment is performed.

In step 112, as the judgment step, the judgment unit 380 judges whether the calculated parallel shift amounts $(x_0, y_0)$, the calculated expansion and contraction error coefficients $(\delta x, \delta y)$, the calculated rotation error coefficients $(\theta, \phi)$, the calculated gray-level offset $\epsilon 0$ and the calculated image transmission loss ratio $\epsilon_1$ are suitable or unsuitable, by using each threshold value set up for each of them. For example, if each of the parallel shift amounts $(x_0, y_0)$ is one pixel or less, it is judged to be "suitable", and if it is more than one pixel, it is judged to be "unsuitable". Similarly, if each of the absolute values of the expansion and contraction error coefficients ($\delta x$, $\delta y$) indicates an expansion and contraction amount which corresponds to one pixel or less, it is judged to be "suitable", and if the amount corresponds to more than one pixel, it is judged to be "unsuitable". Similarly, if each of the absolute values of the rotation error coefficients ($\theta$, $\phi$) indicates a rotation amount which corresponds to one pixel or less, it is judged to be "suitable", and if the amount corresponds to more than one pixel, it is judged to be "unsuitable". Similarly, if each of the absolute values of the gray-level offset $\epsilon 0$ and the image transmission loss ratio $\epsilon_1$ indicates an amount which corresponds to one pixel or less, it is judged to be "suitable", and if the amount is more than one pixel, it is judged to be "unsuitable". However, these threshold values are not restricted to one pixel or the amount corresponding to one pixel, and they can be suitably selected if needed. When all of the judgment results of all the parameters are "suitable", it goes to step 116. When there is at least one parameter judged to be "unsuitable", it goes to step 114.

In step 114, as the least-squares method parameter recalculation step, the least-squares method parameter recalculation unit 382 deletes a parameter or parameters regarded to be "unsuitable" as the judgment result or sets up a value equivalent to deletion for the parameter or the parameters, and then recalculates the other parameters in the model equation (5) by using the least-squares method. In order to obtain a stable solution depending upon a pattern, a normal or "regular" matrix A for the least-squares method needs to be degenerated and deformed to A' so as not to be rank deficient. Therefore, when the absolute value of a specific parameter value exceeds a threshold value previously set up, what is necessary is to delete a term (or terms) related to the specific parameter or to recalculate the other parameters while defining the value of the specific parameter to be a fixed value "0". As mentioned above, it is possible to obtain a stable solution by deleting such a specific parameter. In other words, it is possible to reduce the instability of a calculation result.

In step 116, as the corrected image generation step, the corrected image generation circuit 390, based on each calculated parameter, generates corrected image data by shifting the position of the reference data from the position sparsely aligned by a pixel unit according to the SSD alignment to a position shifted by a displacement amount. Moreover, when a recalculation has been performed after deleting a part of the parameters, the corrected image generation circuit 390, based on the recalculated parameters, generates corrected image data by shifting the position of the reference data from the position sparsely aligned by a pixel unit according to the SSD alignment to a position shifted by a displacement amount.

For example, the corrected image data is herein generated by performing a linear interpolation in the 4-point weighted model. First, the displacement amount calculation unit 392 calculates a displacement amount (x', y') at an arbitrary coordinates (x, y) in each frame, based on the following equations (7-1) and (7-2), for example.

$$x'(x,y) = x_0 - X \cdot \delta_x + y \cdot \theta \quad (7\text{-}1)$$

$$y'(x,y) = y_0 - y \cdot \delta_y - x \cdot \phi \quad (7\text{-}2)$$

The displacement amounts to be corrected at the four corners $(-\frac{1}{2}, \frac{1}{2})$, $(\frac{1}{2}, \frac{1}{2})$, $(\frac{1}{2}, -\frac{1}{2})$, and $(-\frac{1}{2}, -\frac{1}{2})$ of a standardized frame can be calculated by substituting the displacement amount (x', y') at an arbitrary coordinates (x, y) in the following equations (8-1) to (8-5). Thus, the displacement amount of the reference data can be expressed by performing a linear interpolation according to the coordinates (x, y) in the frame.

$$(x_1, y_1) = (x'(-\tfrac{1}{2}, -\tfrac{1}{2}), y'(-\tfrac{1}{2}, -\tfrac{1}{2})) \quad (8\text{-}1)$$

$$(x_2, y_2) = (x'(\tfrac{1}{2}, -\tfrac{1}{2}), y'(\tfrac{1}{2}, -\tfrac{1}{2})) \quad (8\text{-}2)$$

$$(x_3, y_3) = (x'(\tfrac{1}{2}, \tfrac{1}{2}), y'(\tfrac{1}{2}, \tfrac{1}{2})) \quad (8\text{-}3)$$

$$(x_4, y_4) = (x'(-1/2, 1/2), y'(-1/2, 1/2)) \quad (8\text{-}4)$$

The image generation unit 394 generates corrected image data by calculating a pixel value U'(x, y) of a corrected image. The pixel value U' (x, y) can be calculated by substituting the obtained displacement amounts $(x_1, y_1), (x_2, y_2), (x_3, y_3)$, and $(x_4, y_4)$ at the four corners of a frame, a gray-level offset $\epsilon 0$, an image transmission loss ratio $\epsilon_1$, and a pixel value U(x, y) of the reference image in the following equation (9).

$$U'(x, y) = \varepsilon_0 + (1 - \varepsilon_1) \cdot \{(1-x) \cdot (1-y) \cdot U(x - x_1, y - y_1) + \quad (9)$$
$$x \cdot (1-y) \cdot U(x - x_2, y - y_2) +$$
$$x \cdot y \cdot U(x - x_3, y - y_3) + (1-x) \cdot y \cdot U(x - x_4, y - y_4)\}$$

The corrected image data generated as mentioned above is output to the comparison circuit 108. Then, the measurement data is also output to the comparison circuit 108.

In step 118, as the comparison step, the comparison circuit 108 imports the measurement data serving as a pattern image to be inspected and the corrected image data serving as an inspection reference pattern image. The imported measurement data and corrected image data are compared according to a predetermined algorithm and judged whether there is a defect in them or not. Then, the comparison result is output. As mentioned above, by using the corrected image in which systematic position error factors, such as stage meandering, an error due to expansion and contraction, and an inclination error with respect to the running axis of the camera, have been corrected except for pattern defective parts, it becomes possible to perform highly accurate position alignment. Thus, owing to comparing data in which such a highly precise alignment has been performed, a false detection of defects can be prevented and pseudo defects can be reduced, thereby performing a highly accurate inspection.

Now, another method is described that performs a position correction of the reference image by using obtained parameter values. Corrected image data can also be calculated by the following model equations (10-1) and (10-2).

$$U'(x, y) = \varepsilon_0 + (1 - \varepsilon_1) \cdot \sum_i \sum_j w_{ij} \cdot U(x - x_i, y - y_j) \quad (10\text{-}1)$$

$$w_{ij} = \begin{cases} 1 & (|x - x_i| < 1/2N, |y - y_j| < 1/2N) \\ 0 & (\text{if otherwise}) \end{cases} \quad (10\text{-}2)$$

In this case, a corrected image is generated by performing a linear interpolation in the model which simply divides an image frame of a predetermined size into N×N. Dividing the image frame into blocks of N by N, a displacement amount $(x_i, y_j)$ at the coordinates (i, j) in each block is calculated by the following equation (11). The displacement amount $(x_i, y_j)$ obtained by the equation (11) can be applied with respect to all the coordinates in the block.

$$(x_i, y_j) = (x'(i/N, j/N), y'(i/N, j/N)) \quad (11)$$

As can be seen from the above description, it is possible to suitably obtain corrected image data.

In each of the Embodiments mentioned above, with the configuration of FIG. 1, the photodiode array 105 which simultaneously inputs beams corresponding to the number of pixels (for example, 2048 pixels) having the scanning width W is employed, but not limited thereto.

Figure 6:
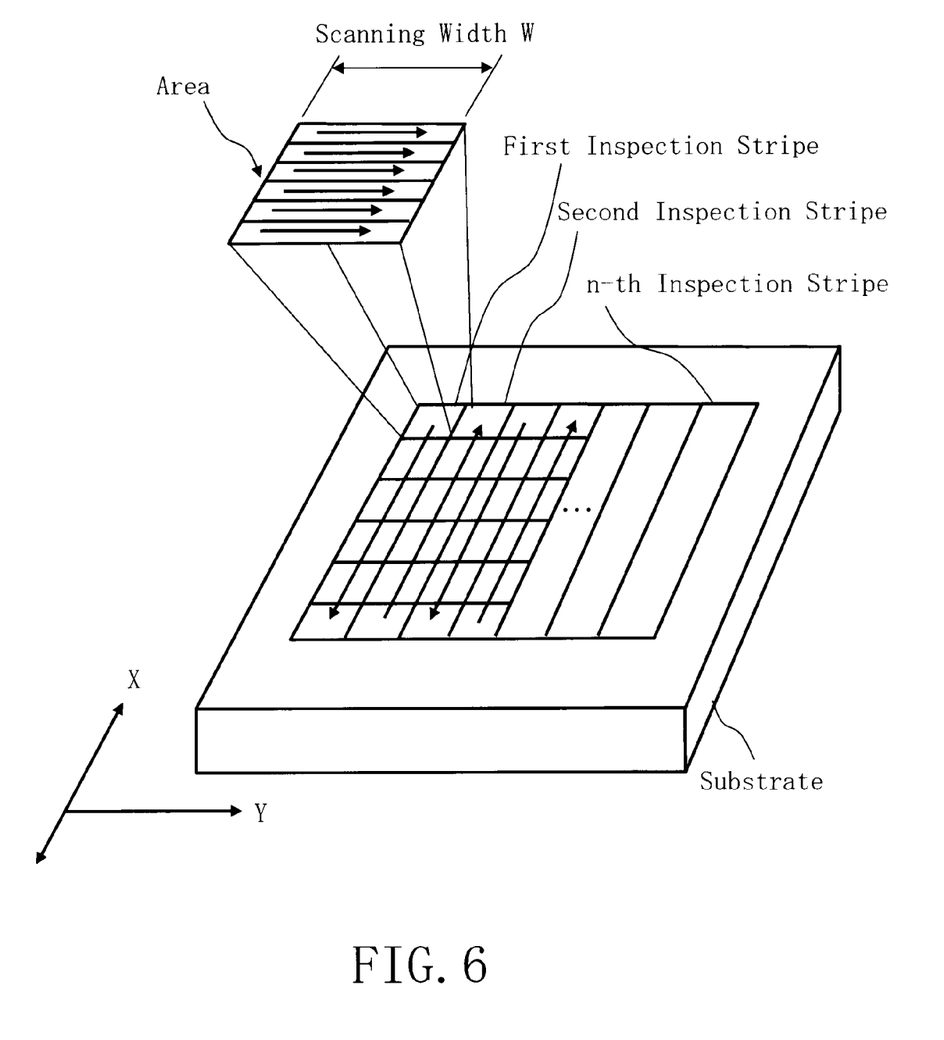
FIG. 6 is a diagram for explaining another method for acquiring an optical image.

FIG. 6 is a diagram for explaining another method for acquiring an optical image. According to this method, as shown in FIG. 6, while the XYθ table 102 is transferred at a constant speed in the X direction, a laser scanning optical device (not shown) scans with a laser beam in the Y direction at every time when detecting a movement of a specific pitch by a laser interferometer, and acquires a two-dimensional image in every area of a predetermined size by way of detecting transmitted lights.

In the Embodiment mentioned above, it is possible to obtain parameters by using the model in which the number of parameters is decreased. Therefore, the operation time can be shortened, and furthermore the instability of the calculation result can be reduced. Accordingly, inspection can be performed highly sensitively.

In the above explanation, what is described as a "unit", "circuit" or "step" can be configured by a computer-executable program. They may be executed by a software program or by any combination of software, hardware and/or firmware. Alternatively, they may be configured by hardware. When the units, the circuits and the steps are configured by programs, the programs are recordable on a recording medium, such as a magnetic disk drive 109, a magnetic tape drive 115, an FD or a ROM (read only memory, not shown). For example, the table control circuit 114, the reference circuit 112, the comparison circuit 108, the position alignment circuit 140, the respective units and circuits in the position alignment circuit 140, and the like that constitute an operation control unit may be configured by electric circuits. Alternatively, they may be executed as software to be processed by the control calculator 110, or executed by a combination of electric circuits and software.

The embodiments have been described above with reference to the concrete examples. However, the present invention is not limited to these concrete examples. For example, although transmitted light is used in the embodiments, reflected light may also be used, or transmitted light and reflected light may be used simultaneously. The reference image is generated from design data, but alternatively, data of the same pattern whose image is captured by a sensor such as a photodiode array may be employed. In other words, it is equally preferable to employ the die to die inspection or the die to database inspection.

Moreover, although apparatus configurations, control methods, and the like which are not directly required in explaining the present invention are not described, a necessary apparatus configuration, a necessary control method, etc. can be appropriately selected and used if needed.

Furthermore, all pattern inspection apparatuses, pattern inspection methods, image position alignment methods, and positional displacement estimation methods that have the elements of the present invention and that can be appropriately modified in design by a person skilled in the art are included in the spirit and scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus having a microprocessor comprising:

an optical image acquisition unit configured to acquire an optical image of a target workpiece to be inspected on which a pattern is formed;

a reference image generation unit configured to generate a reference image to be compared with the optical image;

a least-squares method calculation unit configured, by using a mathematical model in which a parallel shift amount displaced from a position where the optical image and the reference image are aligned by a pixel unit, an expansion and contraction error coefficient, a rotation error coefficient, a gray-level offset and an image transmission loss ratio are parameters, to calculate each of the parameters by a least-squares method;

a corrected image generation unit configured to generate a corrected image by shifting a position of the reference image by a displacement amount displaced from the position aligned by the pixel unit, based on the each of the parameters; and a comparison unit implemented by the microprocessor and configured to compare the corrected image with the optical image, wherein the least-squares method calculation unit calculates a gray-level offset, an image transmission loss ratio, a parallel shift amount in X direction, a parallel shift amount in Y direction, an expansion and contraction error coefficient in the X direction, an expansion and contraction error coefficient in the Y direction, a rotation error coefficient in the X direction, and a rotation error coefficient of the Y direction so that a first difference obtained by subtracting a second sum that is a sum of a product of the expansion and contraction error coefficient in the X direction, a value obtained by partially differentiating a pixel value of the reference image with respect to x, and a variable x, a product of the expansion and contraction error coefficient in the Y direction, a value obtained by partially differentiating the pixel value of the reference image with respect to y, and a variable y, and a product of the rotation error coefficient in the Y direction, the value obtained by partially differentiating the pixel value of the reference image with respect to y, and the variable x from a first sum that is a sum of the gray-level offset, a product of the image transmission loss ratio and the pixel value of the reference image, a product of the parallel shift amount in the X direction and the value obtained by partially differentiating the pixel value of the reference image with respect to x, a product of the parallel shift amount in the Y direction and the value obtained by partially differentiating the pixel value of the reference image with respect to y, and a product of the rotation error coefficient in the X direction, the value obtained by partially differentiating the pixel value of the reference image with respect to x, and the variable y may be equal to a second difference obtained by subtracting a pixel value of the optical image from the pixel value of the reference image.

2. The apparatus according to claim 1, wherein the corrected image generation unit generates the corrected image by performing a linear interpolation in a 4-point weighted model.

3. The apparatus according to claim 1, wherein the corrected image generation unit generates the corrected image by performing a linear interpolation in a model which simply divides an image of a predetermined size into N×N.

4. The apparatus according to claim 1, wherein the least-squares method calculation unit is implemented by the microprocessor.

5. A pattern inspection apparatus having a microprocessor comprising:

an optical image acquisition unit configured to acquire an optical image of a target workpiece to be inspected on which a pattern is formed;

a reference image generation unit configured to generate a reference image to be compared with the optical image;

a least-squares method calculation unit configured, by using a mathematical model in which a parallel shift amount displaced from a position where the optical image and the reference image are aligned by a pixel unit, an expansion and contraction error coefficient, a rotation error coefficient, a gray-level offset and an image transmission loss ratio are parameters, to calculate each of the parameters by a least-squares method;

a judgment unit configured to judge whether a calculated parallel shift amount, a calculated expansion and contraction error coefficient, a calculated rotation error coefficient, a calculated_gray-level offset and a calculated image transmission loss ratio are suitable or unsuitable, by using each threshold value set up for each of the parameters;

a second least-squares method calculation unit configured to delete at least one parameter judged to be unsuitable or set up a value equivalent to deletion for the parameter judged to be unsuitable, and recalculate other parameters in the mathematical model by the least-squares method;

a corrected image generation unit configured to generate a corrected image by shifting a position of the reference image by a displacement amount displaced from the position aligned by the pixel unit, based on recalculated parameters; and a comparison unit implemented by the microprocessor and configured to compare the corrected image with the optical image, wherein the least-squares method calculation unit calculates a gray-level offset, an image transmission loss ratio, a parallel shift amount in X direction, a parallel shift amount in Y direction, an expansion and contraction error coefficient in the X direction, an expansion and contraction error coefficient in the Y direction, a rotation error coefficient in the X direction, and a rotation error coefficient of the Y direction so that a first difference obtained by subtracting a second sum that is a sum of a product of the expansion and contraction error coefficient in the X direction, a value obtained by partially differentiating a pixel value of the reference image with respect to x, and a variable x, a product of the expansion and contraction error coefficient in the Y direction, a value obtained by partially differentiating the pixel value of the reference image with respect to y, and a variable y, and a product of the rotation error coefficient in the Y direction, the value obtained by partially differentiating the pixel value of the reference image with respect to y, and the variable x from a first sum that is a sum of the gray-level offset, a product of the image transmission loss ratio and the pixel value of the reference image, a product of the parallel shift amount in the X direction and the value obtained by partially differentiating the pixel value of the reference image with respect to x, a product of the parallel shift amount in the Y direction and the value obtained by partially differentiating the pixel value of the reference image with respect to y, and a product of the rotation error coefficient in the X direction, the value obtained by partially differentiating the pixel value of the reference image with respect to x, and the variable y may be equal to a second difference obtained by subtracting a pixel value of the optical image from the pixel value of the reference image.

6. The apparatus according to claim 5, wherein the corrected image generation unit generates the corrected image by performing a linear interpolation in a 4-point weighted model.

7. The apparatus according to claim 5, wherein the corrected image generation unit generates the corrected image by performing a linear interpolation in a model which simply divides an image of a predetermined size into N×N.

8. The apparatus according to claim 5, wherein the least-squares method calculation unit is implemented by the microprocessor.

9. A corrected image generation method implemented by a pattern inspection apparatus having a microprocessor comprising:

inputting an optical image and a reference image of a target workpiece to be inspected;

calculating, by using a mathematical model in which a parallel shift amount displaced from a position where the optical image and the reference image are aligned by a pixel unit, an expansion and contraction error coefficient, a rotation error coefficient, a gray-level offset and an image transmission loss ratio are parameters, the parameters by a least-squares method; and generating, using the microprocessor, a corrected image by shifting a position of the reference image by a displacement amount displaced from the position aligned by the pixel unit, based on calculated parameters, and outputting the corrected image, wherein a gray-level offset, an image transmission loss ratio, a parallel shift amount in X direction, a parallel shift amount in Y direction, an expansion and contraction error coefficient in the X direction, an expansion and contraction error coefficient in the Y direction, a rotation error coefficient in the X direction, and a rotation error coefficient of the Y direction are calculated, so that a first difference obtained by subtracting a second sum that is a sum of a product of the expansion and contraction error coefficient in the X direction, a value obtained by partially differentiating a pixel value of the reference image with respect to x, and a variable x, a product of the expansion and contraction error coefficient in the Y direction, a value obtained by partially differentiating the pixel value of the reference image with respect to y, and a variable y, and a product of the rotation error coefficient in the Y direction, the value obtained by partially differentiating the pixel value of the reference image with respect to y, and the variable x from a first sum that is a sum of the gray-level offset, a product of the image transmission loss ratio and the pixel value of the reference image, a product of the parallel shift amount in the X direction and the value obtained by partially differentiating the pixel value of the reference image with respect to x, a product of the parallel shift amount in the Y direction and the value obtained by partially differentiating the pixel value of the reference image with respect to y, and a product of the rotation error coefficient in the X direction, the value obtained by partially differentiating the pixel value of the reference image with respect to x, and the variable y may be equal to a second difference obtained by subtracting a pixel value of the optical image from the pixel value of the reference image.

10. The method according to claim 9, wherein the calculating is performed using the microprocessor.

11. A corrected image generation method implemented by a pattern inspection apparatus having a microprocessor comprising:

inputting an optical image and a reference image of a target workpiece to be inspected;

calculating, by using a mathematical model in which a parallel shift amount displaced from a position where the optical image and the reference image are sparsely aligned by a pixel unit, an expansion and contraction error coefficient, a rotation error coefficient, a gray-level offset and an image transmission loss ratio are parameters, the parameters by a least-squares method;

judging whether a calculated parallel shift amount, a calculated expansion and contraction error coefficient, a calculated rotation error coefficient, a calculated gray-level offset and a calculated image transmission loss ratio are suitable or unsuitable by using each threshold value set up for each of the parameters;

deleting at least one parameter judged to be unsuitable or setting up a value equivalent to deletion for the parameter judged to be unsuitable, and recalculating other parameters in the mathematical model by a least-squares method; and generating, using the microprocessor, a corrected image by shifting a position of the reference image by a displacement amount displaced from the position aligned by the pixel unit, based on recalculated parameters, and outputting the corrected image, wherein a gray-level offset, an image transmission loss ratio, a parallel shift amount in X direction, a parallel shift amount in Y direction, an expansion and contraction error coefficient in the X direction, an expansion and contraction error coefficient in the Y direction, a rotation error coefficient in the X direction, and a rotation error coefficient of the Y direction are calculated, so that a first difference obtained by subtracting a second sum that is a sum of a product of the expansion and contraction error coefficient in the X direction, a value obtained by partially differentiating a pixel value of the reference image with respect to x, and a variable x, a product of the expansion and contraction error coefficient in the Y direction, a value obtained by partially differentiating the pixel value of the reference image with respect to y, and a variable y, and a product of the rotation error coefficient in the Y direction, the value obtained by partially differentiating the pixel value of the reference image with respect to y, and the variable x from a first sum that is a sum of the gray-level offset, a product of the image transmission loss ratio and the pixel value of the reference image, a product of the parallel shift amount in the X direction and the value obtained by partially differentiating the pixel value of the reference image with respect to x, a product of the parallel shift amount in the Y direction and the value obtained by partially differentiating the pixel value of the reference image with respect to y, and a product of the rotation error coefficient in the X direction, the value obtained by partially differentiating the pixel value of the reference image with respect to x, and the variable y may be equal to a second difference obtained by subtracting a pixel value of the optical image from the pixel value of the reference image.

12. The method according to claim 11, wherein the calculating is performed using the microprocessor.

13. A non-transitory computer-readable recording medium storing a program that when executed by a computer causes the computer to implement a method comprising:

storing an optical image and a reference image to be used for a comparative inspection of a target workpiece to be inspected on which a pattern is formed, in a storage device;

reading the optical image and the reference image from the storage device, and by using a mathematical model in which a parallel shift amount displaced from a position where the optical image and the reference image are aligned by a pixel unit, an expansion and contraction error coefficient, a rotation error coefficient, a gray-level offset and an image transmission loss ratio are parameters, calculating the parameters by a least-squares method; and generating a corrected image by shifting a position of the reference image by a displacement amount displaced from the position aligned by the pixel unit, based on the parameters, and outputting the corrected image, wherein a gray-level offset, an image transmission loss ratio, a parallel shift amount in X direction, a parallel shift amount in Y direction, an expansion and contraction error coefficient in the X direction, an expansion and contraction error coefficient in the Y direction, a rotation error coefficient in the X direction, and a rotation error coefficient of the Y direction are calculated, so that a first difference obtained by subtracting a second sum that is a sum of a product of the expansion and contraction error coefficient in the X direction, a value obtained by partially differentiating a pixel value of the reference image with respect to x, and a variable x, a product of the expansion and contraction error coefficient in the Y direction, a value obtained by partially differentiating the pixel value of the reference image with respect to y, and a variable y, and a product of the rotation error coefficient in the Y direction, the value obtained by partially differentiating the pixel value of the reference image with respect to y, and the variable x from a first sum that is a sum of the gray-level offset, a product of the image transmission loss ratio and the pixel value of the reference image, a product of the parallel shift amount in the X direction and the value obtained by partially differentiating the pixel value of the reference image with respect to x, a product of the parallel shift amount in the Y direction and the value obtained by partially differentiating the pixel value of the reference image with respect to y, and a product of the rotation error coefficient in the X direction, the value obtained by partially differentiating the pixel value of the reference image with respect to x, and the variable y may be equal to a second difference obtained by subtracting a pixel value of the optical image from the pixel value of the reference image.

* * * * *